United States Patent [19]

Loeliger

[11] 4,326,055

[45] Apr. 20, 1982

[54] STILBENE DERIVATIVES

[75] Inventor: Peter Loeliger, Kaiseraugst, Switzerland

[73] Assignee: Hoffmann-La Roche Inc., Nutley, N.J.

[21] Appl. No.: 969,907

[22] Filed: Dec. 15, 1978

Related U.S. Application Data

[63] Continuation-in-part of Ser. No. 899,427, Apr. 24, 1978, Pat. No. 4,193,931.

[30] Foreign Application Priority Data

Dec. 22, 1977 [LU] Luxembourg ............................ 78751
Nov. 10, 1978 [CH] Switzerland ....................... 11590/78

[51] Int. Cl.$^3$ ...................... C07C 69/76; C09B 23/00; C09B 55/00
[52] U.S. Cl. .................................. 542/429; 568/426; 568/442; 544/170; 568/631; 568/632; 544/175; 568/633; 568/659; 544/176; 568/661; 568/662; 544/59; 568/663; 568/807; 544/386; 568/808; 570/183; 546/225; 564/134; 564/139; 548/215; 424/246; 424/248.4; 260/410.9 R; 424/248.53; 424/248.57; 260/326.4; 424/263; 424/267; 260/326.8; 424/274; 424/282; 260/338; 424/308; 260/340.3; 260/340.5 R; 560/8; 560/64; 560/65; 560/100; 560/254; 560/255; 562/405; 562/466; 562/473; 562/474; 562/490; 568/10; 568/11; 568/327; 568/328; 568/329; 568/330; 568/306; 568/425
[58] Field of Search ................. 560/100, 8, 64, 65, 560/254, 255; 562/490, 473, 474, 405, 466; 568/442, 425, 426, 662, 663, 10, 11, 807, 808, 327, 328, 329, 330, 659, 661, 631, 632, 633, 306; 542/429; 544/170, 175, 176, 386, 59; 260/338, 340.3, 340.5, 326.4, 326.8; 546/225; 424/308, 246, 248.4, 267, 274, 282

Primary Examiner—Paul J. Killos
Attorney, Agent, or Firm—Jon S. Saxe; George M. Gould; William H. Epstein

[57] ABSTRACT

This invention is directed to 5,6,7,8-tetrahydro-naphthyl or indanyl stilbene derivatives which are useful as tumor inhibiting agents, in the treatment of neoplasms, dermatological conditions and rheumatic illnesses.

47 Claims, No Drawings

STILBENE DERIVATIVES

CROSS REFERENCE TO RELATED APPLICATIONS

This application is a continuation-in-part application of U.S. patent application Ser. No. 899,427 filed Apr. 24, 1978, now U.S. Pat. No. 4,193,931.

SUMMARY

The stilbene derivatives provided by the present invention are compounds of the general formula:

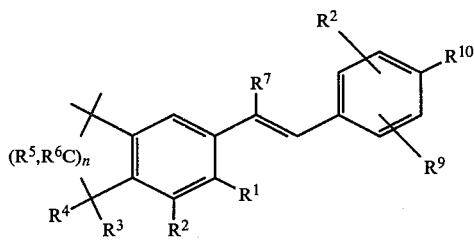

wherein n is an integer of from 1 and 2 and, when n is 1, $R^1$ and $R^2$ are individually hydrogen, lower alkoxy or halogen, or, when n is 2, $R^1$ is hydrogen, lower alkoxy or halogen and $R^2$ is hydrogen; $R^3$, $R^4$, $R^5$ and $R^6$ are individually hydrogen or lower alkyl; $R^7$ is hydrogen, methyl or ethyl; $R^8$ and $R^9$ are hydrogen, lower alkyl or halogen; and $R^{10}$ is $-(CH{=}CR^{19})_mR^{11}$; m is zero or 1; $R^{11}$ is

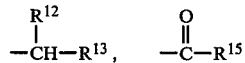

or 2-oxazolinyl, or, when m is 1, $R^{11}$ is additionally hydrogen; $R^{12}$ is hydrogen or lower alkyl; $R^{13}$ is hydrogen, lower alkyl, $-N(R^{17}, R^{18})$ or $-OR^{14}$; $R^{14}$ is hydrogen, lower alkyl or alkanoyl; $R^{15}$ is hydrogen, lower alkyl, $-OR^{16}$ or $-(CH_2)_pN(R^{17}, R^{18})$; $R^{16}$ is hydrogen, lower alkyl, hydroxy-(lower alkyl), aryl, substituted aryl, aralkyl or aralkyl substituted in the aryl portion; $R^{17}$ and $R^{18}$ are individually hydrogen or lower alkyl or $R^{17}$ and $R^{18}$ taken together with the nitrogen atom to which they are attached form a heterocyclic group; $R^{19}$ is hydrogen or lower alkyl and p is zero, 1, 2 or 3; as well as ketals thereof where $R^{11}$ is $-C(O)R^{15}$ and $R^{15}$ is hydrogen or lower alkyl, and salts thereof.

These compounds are useful as tumor inhibiting agents as well as in the treatment of neoplasms, dermatological conditions and rheumatic illnesses.

DETAILED DESCRIPTION

As used in this specification, the term "lower" means that the groups qualified thereby contain from 1 to 6 carbon atoms.

Alkyl and alkoxy groups can be straight-chain or branched-chain, examples of alkyl groups being the methyl, ethyl, isopropyl and 2-methylpropyl groups and examples of alkoxy groups being the methoxy, ethoxy and isopropoxy groups. Alkanoyl groups are derived, for example, from alkanoic acid containing from 2 to 7 carbon atoms such as acetic acid, propionic acid or pivalic acid, as well as from higher carboxylic acid containing 8 to 20 carbon atoms (e.g. from palmitic acid or stearic acid). The phenyl group is a preferred aryl group. Examples of substituted aryl groups are hydroxy-, nitro- and halo-phenyl groups. The benzyl group is a preferred aralkyl group. Examples of heterocyclic groups denoted by $-N(R^{17}, R^{18})$ are 5-membered or 6-membered nitrogen-containing heterocyclic rings which may contain either oxygen or sulphur hetero atom or an additional nitrogen hetero atom (e.g. the piperidino, piperazino, morpholino, thiamorpholino and pyrrolidino groups). Examples of ketals are di(lower alkyl) ketals and lower alkylene ketals. The oxazolinyl group can be substituted by one or two lower alkyl groups. Of the halogen atoms, chlorine and bromine are preferred.

A preferred class of compounds of formula I hereinbefore comprises those in which, when n stands for 1, $R^1$ and $R^2$ represent hydrogen, lower alkoxy or halogen, or, when n stands for 2, $R^1$ represents hydrogen, lower alkoxy or halogen and $R^2$ represents hydrogen; $R^3$, $R^4$, $R^5$ and $R^6$ represent hydrogen or lower alkyl; $R^7$ represents hydrogen, methyl or ethyl; $R^8$ and $R^9$ represent hydrogen, lower alkyl or halogen; and $R^{10}$ represents hydroxymethyl, alkoxymethyl, alkanoyloxymethyl, carboxyl, alkoxycarbonyl, formyl, alkylenedioxymethyl, alkanoyl, carbamoyl, mono(lower alkyl)-carbamoyl, di(lower alkyl)carbamoyl, N-heterocyclylcarbonyl or 2-oxazolinyl. Furthermore, compounds of formula I in which n stands for 2 are preferred, as are compounds of formula I in which $R^1$, $R^2$, $R^5$, $R^6$, $R^8$ and $R^9$ represent hydrogen and $R^3$, $R^4$ and $R^7$ represent methyl. A further preferred class of compounds of formula I comprises those in which $R^{10}$ represents a group of the formula $-(CH{=}CH)_mR^{11}$, especially when m stands for zero and, moreover, when $R^{11}$ represents lower alkoxycarbonyl, lower alkylcarbamoyl, lower alkoxymethyl or lower alkanoyloxymethyl.

According to the process provided by the present invention, the stilbene derivatives aforesaid (i.e. the compounds of formula I and their salts) are manufactured by reacting a compound of the general formula

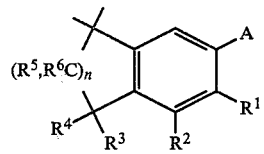

with a compound of the general formula

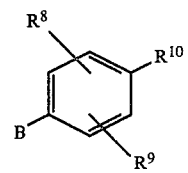

wherein $R^1$, $R^2$, $R^3$, $R^4$, $R^5$, $R^6$, $R^8$, $R^9$, $R^{10}$ and n are as above; and either A is a triarylphosphonium alkyl group of the formula

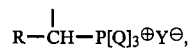

R is hydrogen, methyl or ethyl; Q is aryl; Y is an anion of an organic or inorganic acid; and B is formyl; or A is formyl, acetyl or propionyl and B is a dialkoxyphosphinylalkyl group of the formula

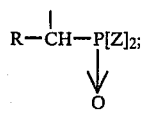

R is hydrogen, methyl and ethyl; and Z is lower alkoxy;

to give a compound of formula I and, if desired, functionally modifying the group $R^{10}$.

The aryl groups denoted by Q in the aforementioned triarylphosphoniumalkyl groups include all generally known aryl groups, but especially mononuclear aryl groups such as phenyl, lower alkyl-substituted phenyl or lower alkoxy-substituted phenyl (e.g. tolyl, xylyl, mesityl and p-methoxyphenyl). Of the inorganic acid anions denoted by Y the chloride, bromide and hydrosulphate ions are preferred and of the organic acid anions, the mesyloxy or tosyloxy ions are preferred.

The alkoxy groups denoted by Z in the aforementioned dialkylphosphinylalkyl groups are preferably lower alkoxy groups (i.e. alkoxy groups containing 1–6 carbon atoms such as the methoxy and ethoxy groups).

The starting materials of formula II, insofar as their preparation is not known or described hereinafter, can be prepared according to known methods or in an analogous manner to the methods described hereinafter.

Compounds of formula II in which A represents a formyl, acetyl or propionyl group and $R^1$ and $R^2$ represent hydrogen [oxo compounds of formula II] can be prepared, for example, by subjecting an indane derivative, which is substituted in the cyclopentene ring corresponding to the desired compound of formula I, or a tetrahydronaphthalene derivative, which substituted in the cyclohexene ring corresponding to the desired compound of formula I, to an acylation. This acylation can be carried out, for example, in the presence of a Lewis acid.

Suitable acylating agents are formaldehyde/hydrochloric acid, acetyl halides (e.g. acetyl chloride) and propionyl halides (e.g. propionyl chloride). The preferred Lewis acids are the aluminium halides such as aluminium trichloride. The acylation is conveniently carried out in a solvent, such as nitrobenzene or a chlorinated hydrocarbon such as methylene chloride. The acylation is preferably carried out at a temperature of from 0° C. to about +5° C.

A resulting oxo compound of formula II in which $R^1$ and $R^2$ each represent a hydrogen atom is reacted in accordance with the present invention with a phosphonate of formula III in which B represents a dialkoxyphosphinylalkyl group to give a compound of formula I in which $R^1$ and $R^2$ each represent a hydrogen atom.

The phosphonium salts of formula II in which A represents a 1-(triarylphosphonium)-(methyl or ethyl or propyl) group required for the reaction with an aldehyde of formula III in which B represents an oxo group can be prepared, for example, as follows:

An aforementioned oxo compound of formula II in which $R^1$ and $R^2$ represent hydrogen is reduced to give a corresponding alcohol at about 0° C. to about +5° C. using a complex metal hydride (e.g. sodium borohydride in an alkanol or lithium aluminium hydride in an ether, tetrahydrofuran or dioxan). The resulting alcohol is subsequently halogenated in the presence of an amine base (e.g. pyridine) using a customary halogenating agent (e.g. phosphorus oxychloride or phosphorus tribromide). The halide obtained is then reacted with a triarylphosphine in a solvent, preferably triphenylphosphine in toluene or xylene, to give a desired phosphonium salt of formula II.

Oxo compounds and phosphonium salts of formula II in which $R^1$ and $R^2$ represent alkoxy or halogen can be prepared, for example, by converting a corresponding phenol in a manner known per se into a corresponding alkoxy-substituted derivative of formula II by treatment with an alkylating agent (e.g. a lower alkyl halide or a lower alkanol in the presence of an acid agent).

The aforementioned phenols can be obtained, for example, as follows:

An oxo compound of formula II in which $R^1$ and $R^2$ represent hydrogen is nitrated by treatment with a mixture of concentrated nitric acid and concentrated sulphuric acid. The nitro group which is preferentially introduced in the ortho-position to the formyl, acetyl or propionyl group is catalytically reduced in a manner known per se (e.g. with the aid of Raney-nickel) to the amino group which is replaced by the hydroxy group via the diazonium salt in a known manner.

If the diazonium salt prepared from the amine is treated in the warm with a copper (I) halide, then there is obtained the corresponding halo derivative of the oxo compound of formula II. By treating said halo derivative with nitric acid it is possible to introduce, in the meta-position to the formyl, acetyl or propionyl group, a nitro group which likewise can be replaced in the manner previously described by the hydroxy group or a halogen atom. By converting the hydroxy group into an alkoxy group there can be obtained, if desired, ketones of formula II which carry similar or mixed substitution.

A halogen atom present on the aromatic nucleus can be removed, if desired, by reduction in a manner known per se.

The compounds of formula III in which B represents the formyl group can be prepared from phenyl derivatives which are nitro-substituted in the 1-position in the manner described in Chem. Berichten 102 (1969), pages 2502–2507. They can also be prepared by reducing a corresponding p-carboxy substituted phenyl derivative. The reduction of the carboxyl group to the formyl group can be carried out, for example, with diisobutylaluminium hydride.

The compounds of formula III in which B represents a dialkoxyphosphinylmethyl group can be prepared from the aforementioned compounds of formula III in which B represents the formyl group by converting the formyl group using a metal hydride (e.g. sodium borohydride) into the hydroxymethyl group, halogenating the hydroxymethyl group using a customary halogenating agent (e.g. phosphorus trichloride) and reacting the resulting halomethyl group with a trialkylphosphite, especially triethylphosphite, to give a desired phosphonate of formula III.

A compound of formula III in which B represents the formyl group or a dialkoxyphosphinylmethyl group can be prepared by halogenating a corresponding phenyl derivative which is methyl-substituted in the 1-position and either reacting the resulting halomethyl derivative with a trialkylphosphite or hydrolysing said halomethyl derivative to the hydroxymethyl derivative and oxidising the latter by treatment with an oxidising agent (e.g. manganese dioxide).

The reaction of a compound of formula II with a compound of formula III in accordance with the process provided by the present invention can be carried out according to the known methods of the Wittig reaction or the Horner reaction. There are preferably used as the starting materials those compounds of formula III in which $R^{11}$ represents a group which is not reactive towards phosphoranes such as, in particular, the formyl group.

The functional modification of a group $R^{10}$, also in accordance with the process provided by the present invention, can comprise, for example, the conversion of the carboxyl group into a salt, an ester, an amide, an oxaline derivative or into the hydroxymethyl group which can subsequently be etherified or esterified. Another functional modification comprises the saponification of a carboxylic acid ester or the reduction thereof to the hydroxymethyl group. The hydroxymethyl group can also be oxidised to the formyl group. Compounds of formula I which contain a formyl group can be converted, e.g. by means of a Wittig reaction, into compounds of formula I in which $R^{10}$ represents a group of the formula $-(CH=CR^{19})_mR^{11}$ in which m stands for 1, $R^{19}$ represents hydrogen or alkyl and $R^{11}$ represents alkoxymethyl, alkanoyloxymethyl, carboxyl, alkoxycarbonyl, alkanyl or alkenyl. All of these functional modifications can be carried out according to methods known per se.

In the case of the Wittig reaction, the starting materials are reacted with one another in the presence of an acid binding agent, for example, in the presence of a strong base such as butyl lithium, sodium hydride or the sodium salt of dimethyl sulphoxide, but preferably in the presence of an ethylene oxide which is optionally substituted by lower alkyl such as 1,2-butylene oxide, if desired in a solvent (e.g. an ether, such as diethyl ether or tetrahydrofuran or an aromatic hydrocarbon such as benzene) at a temperature between room temperature and the boiling point of the reaction mixture.

In the case of the Horner reaction, the starting materials are reacted with one another in the presence of a base and, preferably, in the presence of an inert organic solvent; for example, in the presence of sodium hydride in benzene, toluene, dimethylformamide, tetrahydrofuran, dioxan or 1,2-dimethoxyalkane or in the presence of a sodium alcoholate in an alkanol (e.g. sodium methylate in methanol) at a temperature between 0° C. and the boiling point of the reaction mixture.

It has been found to be convenient in certain cases to carry out the aforementioned reactions in situ, i.e. to react the starting materials with one another without isolating the phosphonium salt or phosphonate in question from the medium in which it is prepared.

A carboxylic acid of formula I can be converted in a manner known per se (e.g. by treatment with thionyl chloride, preferably in pyridine, or phosphorus trichloride in toluene) into an acid chloride which can be converted by reaction with an alcohol into an ester or by reaction with an amine into a corresponding amide. Amides can be converted into amines in a manner known per se; for example, by reduction with complex metal hydrides such as lithium aluminium hydride.

A carboxylic acid ester of formula I can be hydrolysed in a manner known per se (e.g. by treatment with alkali, especially by treatment with aqueous-alcoholic sodium hydroxide or potassium hydroxide) at a temperature between room temperature and the boiling point of the mixture and the resulting carboxylic acid can then be amidated via an acid halide as described earlier. Alternatively, a carboxylic acid ester of formula I can be directly amidated as described hereinafter.

A carboxylic acid ester of formula I can be converted directly into a corresponding amide, for example by treatment with lithium amide. The ester is advantageously treated with lithium amide at room temperature.

A carboxylic acid of formula I can be converted into an oxazoline derivative of formula I via a halide by reaction with 2-aminoethanol or 2-amino-2-methyl-1-propanol and subsequent cyclisation.

A carboxylic acid or carboxylic acid ester of formula I can be reduced in a manner known per se to give a corresponding alcohol of formula I. The reduction is advantageously carried out using a metal hydride or alkyl metal hydride in an inert solvent. Especially suitable hydrides are the mixed metal hydrides such as lithium aluminium hydride or bis[methoxy-ethylenoxy]-sodium aluminium hydride. Suitable solvents are, inter alia, ether, tetrahydrofuran or dioxan when lithium aluminium hydride is used and ether, hexane, benzene or toluene when diisobutylaluminium hydride or bis[methoxy-ethylenoxy]-sodium aluminium hydride is used.

An alcohol of formula I can be etherified with an alkyl halide (e.g. methyl iodide), for example, in the presence of a base, preferably sodium hydride, in an organic solvent such as dioxan, tetrahydrofuran, 1,2-dimethoxyethane or dimethylformamide, or in the presence of an alkali metal alcoholate in an alkanol, at a temperature between 0° C. and room temperature.

An alcohol of formula I can be esterified by treatment with an alkanoyl halide or anhydride, conveniently in the presence of a base (e.g. pyridine or triethylamine) at a temperature range between room temperature and the boiling point of the mixture.

A carboxylic acid of formula I forms salts with bases, especially with alkali metal hydroxides and preferably with sodium hydroxide or potassium hydroxide.

The compounds of formula I occur predominantly in the trans form. Cis isomers which may be obtained can be separated or isomerised to the trans isomers in a manner known per se where desired.

The stilbene derivatives provided by the present invention are pharmacodynamically useful. They can be used for the topical and systemic therapy of benign and malignant neoplasms and of premalignant lesions as well as for the systemic and topical prophylaxis of the said conditions.

The present stilbene derivatives are also suitable for the topical and systematic therapy of acne, psoriasis and other dermatoses accompanied by an intensified or pathologically altered cornification, as well as of inflammatory and allergic dermatological conditions. They can moreover be used for the control of mucous membrane diseases associated with inflammatory or degenerative or metaplastic changes.

Compared with known retinoids, the stilbene derivatives provided by this invention are characterised in that they are active in extraordinarily slight amounts.

The tumour-inhibiting activity of the present stilbene derivatives is significant. In the papilloma test in mice, tumours induced with dimethylbenzanthracene and croton oil regress. In the case of the intraperitoneal administration of p-[(E)-2-(5,6,7,8-tetrahydro-5,5,8,8-tetramethyl-2-naphthyl)propenyl]-benzoic acid ethyl ester, the diameter of the papilloma decreases in the course of 2 weeks by 75% at a dosage of 0.2 mg/kg/week, by 56% at a dosage of 0.1 mg/kg/week and by 48% at a dosage of 0.05 mg/kg/week. In the case of oral administration of p-[(E)-2-(5,6,7,8-tetrahydro-5,5,8,8-tetramethyl-2-naphthyl)propenyl]-benzoic acid ethyl ester to mice, the diameter of the induced tumours decreases in the course of 2 weeks (5 individual doses/week) by 63% at a dosage of 0.4 mg (5×0.08 mg)/kg/week, by 48% at The stilbene derivatives provided by this invention can also be used for the oral treatment of rheumatic illnesses, especially those of an inflammatory or degenerative kind which attack the joints, muscles, tendons and other parts of the motor apparatus. Examples of such illnesses are rheumatic arthritis, Bechterew's spondylarthritis ankylopoetica and psoriatic arthropathy.

For the treatment of these illnesses, the present stilbene derivatives are administered orally, the dosage in the case of adults conveniently being about 0.01–1 mg/kg body weight per day, preferably 0.05–0.5 mg/kg/day. A possible over-dosage can manifest itself in the form of a vit-A hypervitaminosis which can readily be recognised from its symptoms (scaling of the skin, hair loss).

The dosage can be administered as a single dosage or in several sub-divided dosages.

The stilbene derivatives provided by the present invention can therefore be used as medicaments, for example in the form of pharmaceutical preparations which contain them in association with a carrier material.

The pharmaceutical preparations suitable for systemic administration can be produced, for example, by adding a compound of formula I or a salt thereof as the active ingredient to non-toxic, inert, solid or liquid carriers which are conventionally used in such preparations.

The pharmaceutical preparations can be administered enterally, parenterally or topically. Suitable preparations for enteral administration are, for example, tablets, capsules, dragees, syrups, suspensions, solutions and suppositories. Suitable preparations for parenteral administration are infusion or injection solutions.

The dosages in which the present stilbene derivatives are administered can vary according to the particular dosage form and mode of administration as well as according to the requirements of the patient.

The stilbene derivatives of this invention can be administered in amounts of ca 0.01 mg to ca 5 mg daily in one or more dosages. A preferred form of administration comprises capsules containing ca 0.1 mg to ca 1.0 mg of active ingredient.

The pharmaceutical preparations can contain inert as well as pharmacodynamically active additives. Tablets or granulates, for example, can contain binding agents, filling agents, carrier substances or diluents. Liquid preparations can take the form of, for example, sterile solutions which are miscible with water. Capsules can contain, in addition to the active ingredient, a filling agent or thickening agent. Furthermore, flavour-improving additives, substances normally used as preservatives, stabilisers, wetting agents and emulsifying agents as well as salts for varying the osmotic pressure, buffers and other additives may also be present in the pharmaceutical preparations.

The aforementioned carrier substances and diluents can be organic or inorganic in nature; for example, water, gelatin, lactose, starch, magnesium stearate, talc, gum arabic, polyalkyleneglycols and the like. A prerequisite is that all adjuvants used in the production of the pharmaceutical preparations are non-toxic.

For topical administration, the pharmaceutical preparations are conveniently provided in the form of ointments, tinctures, creams, solutions, lotions, sprays, suspensions and the like. Ointments, creams and solutions are preferred. These pharmaceutical preparations for topical administration can be produced by mixing the present stilbene derivatives with non-toxic, inert, solid or liquid carriers which are customary per se in such preparations and which are suitable for topical administration.

For topical administration there are suitably used ca 0.001% to ca 0.3%, preferably 0.02% to 0.1%, solutions, as well as ca 0.002% to ca 0.5%, preferably ca 0.02%, to ca 0.1%, ointments or creams.

The pharmaceutical preparations may contain an antioxidant (e.g. tocopherol, N-methyl-γ-tocopheramine, butylated hydroxyanisole or butylated hydroxytoluene).

The following Examples illustrate the process provided by the present invention. In the Examples, the ether used is diethyl ether and the solvent mixtures are given as parts by volume.

EXAMPLE 1

300 ml of butylene oxide are added to 30.5 g of [1-(1,1,3,3-tetramethyl-5-indanyl)ethyl]-triphenylphosphonium bromide and 8 g of 4-ethoxycarbonylbenzaldehyde and the mixture is then stirred at 65° C. for 12 hours in an inert gas atmosphere. The resulting clear solution is cooled, introduced into ca 500 ml of ice/water and extracted twice with hexane. The organic extract is extracted three times with methanol/water, dried over sodium sulphate and concentreated under reduced pressure. The residue is purified by adsorption on silica gel using hexane/ether (19:1) for the elution. The p-[(E)-2-(1,1,3,3-tetramethyl-5-indanyl)propenyl]-benzoic acid ethyl ester obtained from the eluate melts at 70°–71° C. after recrystallization from ether/hexane.

The [1-(1,1,3,3-tetramethyl-5-indanyl)ethyl]-triphenylphosphonium bromide used as the starting material can be prepared, for example, as follows:

87.8 g of acetyl chloride are dissolved in 240 ml of nitrobenzene. 149.2 g of aluminium chloride are introduced portionwise into the solution. The mixture is cooled down to 0°–5° C. and then treated dropwise while cooling well with a solution of 195.0 g of 1,1,3,3-tetramethyl-indane in 360 ml of nitrobenzene. The temperature should not rise above 5° C. The mixture is stirred at 0° C. for 15 hours, then introduced into 3 liters of ice/water and extracted with ether. The ether extract is washed twice with a 2-N sodium hydroxide solution and twice with a saturated sodium chloride solution, dried over sodium sulphate and concentrated, firstly in a water-jet vacuum and then in a high vacuum to remove the nitrobenzene. The residual oily (1,1,3,3-tetramethyl-5-indanyl)-methyl ketone boils at 100°–103° C./0.5 Torr.

2.66 g of lithium aluminium hydride are treated with 40 ml of absolute ether. While cooling to 0°–5° C. there are added dropwise within 30 minutes 26 g of 1,1,3,3-tetramethyl-5-indanyl methyl ketone. After a further 30 minutes, the mixture is cautiously treated dropwise with 25 ml of a saturated sodium sulphate solution. The solution is filtered. The filtrate is washed once with a 1-N sodium hydroxide solution and twice with a saturated sodium chloride solution, dried over sodium sulphate and concentrated under reduced pressure to remove the solvent. The residual oily α-1,1,3,3-pentamethyl-5-indane-methanol, which is uniform according to thin-layer chromatography [flow agent: hexane/ether (80:20)], is immediately processed as follows:

24.0 g of α-1,1,3,3-pentamethyl-5-indane-methanol are dissolved in 20 ml of absolute ether and 100 ml of absolute hexane. After the addition of 2 drops of pyridine, the solution is treated dropwise over a period of 30 minutes with 16.2 g of phosphorus tribromide dissolved in 80 ml of absolute hexane. After stirring at 0°–5° C. for a further hour, the product is introduced into ice/water and exhaustively extracted with ether. The ether extract is washed twice with a saturated sodium bicarbonate solution and twice with a sodium chloride solution, dried over sodium sulphate and evaporated under reduced pressure to remove the solvent. The residual oily 5-(1-bromoethyl)-1,1,3,3-tetramethyl-indane, which is uniform according to thin-layer chromatography [flow agent: hexane/ether (95:5)], is immediately processed as follows:

26.3 g of triphenylphosphine are dissolved in 120 ml of xylene. The solution is treated with 30.9 g of 5-(1-bromoethyl)-1,1,3,3-tetramethyl-indane dissolved in 60 ml of xylene. The mixture is warmed to 100° C. while stirring and left at this temperature for 12 hours. The thick-oily 1-(1,1,3,3-tetramethyl-5-indanyl)ethyl-triphenylphosphonium bromide which thereby separates out and which crystallises after seeding melts at 151°–156° C. after recrystallisation from methylene chloride/toluene (crystals contain 0.3 equivalents of toluene).

EXAMPLE 2

2.4 g of 1,1,3,3-tetramethyl-5-indanyl methyl ketone and 3.4 g of 4-[(diethoxyphosphinyl)methyl]-benzoic acid ethyl ester are dissolved in 7 ml of dimethylformamide. The solution is treated dropwise under argon at room temperature while stirring with a sodium ethanolate solution (prepared from 0.33 g of sodium and 7 ml of ethanol) and subsequently stirred at 70° C. for 18 hours. The mixture is subsequently introduced into ice/water and extracted with ether. The ether extract is washed with a saturated sodium chloride solution, dried over sodium sulphate and evaporated under reduced pressure. The residual p-[(E)-2-(1,1,3,3-tetramethyl-5-indanyl)propenyl]-benzoic acid ethyl ester, a brown oil, is purified by adsorption on silica gel using hexane/ether (9:1) for the elution. The ester melts at 70°–71° C. after recrystallisation from hexane/ether.

EXAMPLE 3

In a manner analogous to that described in Example 1, from [1-(5,6,7,8-tetrahydro-5,5,8,8-tetramethyl-2-naphthyl)ethyl]-triphenylphosphonium bromide and 4-ethoxycarbonylbenzaldehyde there can be obtained p-[(E)-2-(5,6,7,8-tetrahydro-5,5,8,8-tetramethyl-2-naphthyl)propenyl]-benzoic acid ethyl ester of melting point 90°–91° C.

The [1-(5,6,7,8-tetrahydro-5,5,8,8-tetramethyl-2-naphthyl)ethyl]-triphenylphosphonium bromide used as the starting material can be prepared in a manner analogous to that described in Example 1, from 5,6,7,8-tetrahydro-5,5,8,8-tetramethyl-naphthalene via (5,6,7,8-tetrahydro-5,5,8,8-tetramethyl-2-naphthyl)methyl ketone, 5,6,7,8-tetrahydro-α-5,5,8,8-pentamethyl-2-naphthalene-methanol and 2-(bromoethyl)-5,6,7,8-tetrahydro-5,5,8,8-tetramethyl-naphthalene.

EXAMPLE 4

In a manner analogous to that described in Example 1, from [1-(3-methoxy-5,6,7,8-tetrahydro-5,5,8,8-tetramethyl-2-naphthyl)ethyl]-triphehylphosphonium bromide and 4-ethoxycarbonyl-benzaldehyde there can be obtained p-[(E)-2-(3-methoxy-5,6,7,8-tetrahydro-5,5,8,8-tetramethyl-2-naphthyl)propenyl]-benzoic acid ethyl ester of melting point 97°–98° C.

The [1-(3-methoxy-5,6,7,8-tetrahydro-5,5,8,8-tetramethyl-2-naphthyl)ethyl]-triphenylphosphonium bromide used as the starting material can be prepared in a manner analogous to that described in Example 1, from 3-methoxy-5,6,7,8-tetrahydro-5,5,8,8-tetramethyl-naphthalene via (3-methoxy-5,6,7,8-tetrahydro-5,5,8,8-tetramethyl-2-naphthyl)methyl ketone, 3-methoxy-5,6,7,8-tetrahydro-5,5,8,8-tetramethyl-2-naphthalene-methanol and 2-(1-bromoethyl)-3-methoxy-5,6,7,8-tetrahydro-5,5,8,8-tetramethyl-naphthalene.

EXAMPLE 5

In a manner analogous to that described in Example 1, from [1-(5,6,7,8-tetrahydro-5,5,8,8-tetramethyl-2-naphthyl)ethyl]-triphenylphosphonium bromide and 3-methyl-4-ethoxycarbonyl-benzaldehyde there can be obtained p-[(E)-2-(5,6,7,8-tetrahydro-5,5,8,8-tetramethyl-2-naphthyl)propenyl]-2-methyl-benzoic acid ethyl ester as a colourless oil which is uniform according to thin-layer chromatography, (Rf=0.6; hexane/15% ether).

The aforementioned 3-methyl-4-ethoxycarbonyl-benzaldehyde can be prepared from 4-nitro-3-methyl-benzoic acid in a manner analogous to that described for the preparation of 2-methyl-4-ethoxycarbonyl-benzaldehyde by Huneck et al in Chem. Ber. 102, 2502–2507 (1969).

EXAMPLE 6

In a manner analogous to that described in Example 1, from [1-(1,1,2,3,3-pentamethyl-5-indanyl)ethyl]-triphenylphosphonium bromide and 4-ethoxycarbonyl-benzaldehyde there can be obtained p-[(E)-2-(1,1,2,3,3,-pentamethyl-5-indanyl)propenyl]-benzoic acid ethyl ester of melting point 79°–80° C.

EXAMPLE 7

In a manner analogous to that described in Example 1, from [1-(7-methoxy-1,1,3,3-tetramethyl-5-indanyl)ethyl]-triphenylphosphonium bromide and 4-ethoxycarbonyl-benzaldehyde there can be obtained p-[(E)-2-(7-methoxy-1,1,3,3-tetramethyl-5-indanyl)-propenyl]-benzoic acid ethyl ester of melting point 72°–73° C.

The [1-(7-methoxy-1,1,3,3-tetramethyl-5-indanyl)ethyl]-triphenylphosphonium bromide used as the starting material can be prepared, for example, as follows:

84.3 g of (1,1,3,3-tetramethyl-5-indanyl) methyl ketone (prepared as described in Example 1) are dissolved in 160 ml of concentrated sulphuric acid and the solution is cooled down to −20° C. At this temperature there is added during 10 minutes the nitrating acid prepared from 40 ml of concentrated nitric acid and 80 ml of concentrated sulphuric acid. After completion of the addition, the thick paste is immediately poured on to ice and extracted twice with ether. The ether extract is washed with a sodium bicarbonate solution and a sodium chloride solution, dried over sodium sulphate and freed from solvent under reduced pressure. The separated (6-nitro-1,1,3,3-tetramethyl-5-indanyl) methyl ketone melts at 111°-112° C. after recrystallisation from ether/hexane.

75.8 g of (6-nitro-1,1,3,3-tetramethyl-5-indanyl) methyl ketone are dissolved in 1500 ml of methanol and the solution is hydrogenated at 45° C. for 48 hours with the aid of 20 g of Raney-nickel. 15 liters of hydrogen are taken up. The solution is then filtered through a filter aid and the solvent is removed under reduced pressure. The separated (6-amino-1,1,3,3-tetramethyl-5-indanyl) methyl ketone melts at 161°-162° C. after recrystallisation from ether/hexane.

113.1 g of (6-amino-1,1,3,3-tetramethyl-5-indanyl) methyl ketone are suspended in 2260 ml of 20% hydrochloric acid and the suspension is cooled down to 0°-5° C. The cold mixture is treated dropwise within 10 minutes with a solution of 33.9 g of sodium nitrite in 115 ml of water and the resulting solution is stirred for 30 minutes. The cold solution is subsequently introduced dropwise over a period of 2 hours while stirring into a solution of 243.2 g of copper (I) chloride in 250 ml of water and 250 ml of concentrated hydrochloric acid, which is warmed to 40°-45° C. The mixture is then cooled down, introduced into ice-water and extracted three times with methylene chloride. The organic extract is washed with a sodium chloride solution, dried over sodium sulphate and freed from solvent under reduced pressure. The residue is purified by adsorption on silica gel using hexane/acetone (19:1) for the elution. The (6-chloro-1,1,3,3-tetramethyl-5-indanyl) methyl ketone obtained from the eluate melts at 69°-71° C. after recrystallisation from hexane/ether.

In an analogous manner, from (6-chloro-1,1,3,3-tetramethyl-5-indanyl) methyl ketone there can be obtained (6-chloro-7-nitro-1,1,3,3-tetramethyl-5-indanyl) methyl ketone of melting point 119°-120° C., and from (6-chloro-7-nitro-1,1,3,3-tetramethyl-5-indanyl) methyl ketone there can be obtained (6-chloro-7-amino-1,1,3,3-tetramethyl-5-indanyl) methyl ketone of melting point 116°-117° C.

21.1 g of (6-chloro-7-amino-1,1,3,3-tetramethyl-5-indanyl) methyl ketone are introduced into 48 ml of concentrated sulphuric acid and, after the warming to 50° C., the mixture is treated slowly with 140 ml of distilled water. After cooling down to 0°-5° C., there is introduced dropwise into the mixture over a period of 45 minutes a solution of 5.5 g of sodium nitrite in 20 ml of water. The resulting cold mixture is introduced dropwise while stirring over a period of 2 hours into a solution, held at 70° C., of 60 ml of water and 60 ml of concentrated sulphuric acid. The mixture is cooled, then introduced into ice-water and extracted three times with ether. The organic phase is washed with a sodium chloride solution, dried over sodium sulphate and freed from solvent under reduced pressure. The residue is purified by adsorption on silica gel using hexane/ether (19:1) for the elution. The (6-chloro-7-hydroxy-1,1,3,3-tetramethyl-5-indanyl) methyl ketone obtained from the eluate melts at 78°-80° C. after recrystallisation from hexane/ether.

4.4 g of (6-chloro-7-hydroxy-1,1,3,3-tetramethyl-5-indanyl) methyl ketone are dissolved in 10 ml of dimethylformamide. The solution is treated first with 1.1 g of potassium hydroxide (dissolved in 1.2 ml of water) and then with 5.5 ml of methyl iodide and the resulting mixture is subsequently stirred at room temperature for 3 hours. The mixture is introduced into ice-water and extracted twice with ether. The organic extract is washed several times with a sodium chloride solution, dried over sodium sulphate and freed from solvent under reduced pressure. The separated (6-chloro-7-methoxy-1,1,3,3-tetramethyl-5-indanyl) methyl ketone melts at 59°-60° C. after recrystallisation.

25 g of (6-chloro-7-methoxy-1,1,3,3-tetramethyl-5-indanyl) methyl ketone are dissolved in ca 200 ml of methanol and, after the addition of 10 g of triethylamine and 2.5 g of 5% palladium/carbon catalyst, the mixture is hydrogenated at room temperature. 1 mol equivalent of hydrogen is taken up over a period of 5 hours. The solution is filtered over Speedex. The filtrate is evaporated. The residue is dissolved in water/ether and extracted several times with ether. The organic extract is washed with sodium chloride solution, dried over sodium sulphate and freed from solvent under reduced pressure. The separated (7-methoxy-1,1,3,3-tetramethyl-5-indanyl) methyl ketone melts at 76°-77° C. after recrystallisation from hexane.

In a manner analogous to that described in Example 1, from (7-methoxy-1,1,3,3-tetramethyl-5-indanyl) methyl ketone via 7-methoxy-α-1,1,3,3-pentamethyl-5-indane-methanol and 5-(1-bromoethyl)-7-methoxy-1,1,3,3-tetramethyl-indane there can be obtained [1-(7-methoxy-1,1,3,3-tetramethyl-5-indanyl)ethyl]-triphenylphosphonium bromide of melting point 209°-210° C.

EXAMPLE 8

In a manner analogous to that described in Example 1, from [(1,1,3,3-tetramethyl-5-indanyl)methyl]-triphenylphosphonium chloride and 4-ethoxycarbonyl-benzaldehyde there can be obtained p-[(E)-2-(1,1,3,3-tetramethyl-5-indanyl)vinyl]-benzoic acid ethyl ester of melting point 151°-152° C.

The [(1,1,3,3-tetramethyl-5-indanyl)methyl]-triphenylphosphonium chloride used as the starting material can be prepared, for example, as follows:

34.2 g of 1,1,3,3-tetramethyl-indane, 150 ml of glacial acetic acid, 300 ml of concentrated hydrochloric acid and 77 ml of formaldehyde solution (35%) are warmed to 75°-78° C. while stirring for 2 hours. A further 7.7 ml of 35% formaldehyde solution are then added dropwise within 10 minutes. The mixture is held at the same temperature for 15 hours, then cooled down, introduced into ca 1 liter of ice-water and exhaustively extracted with toluene. The organic phase is washed neutral with water, dried over sodium sulphate and evaporated under reduced pressure. The resulting crude product, a reddish oil, is distilled over a Vigreux column. The pure 5-chloromethyl-1,1,3,3-tetramethyl-indane boils at 143°-146° C./19 mmHg.

In a manner analogous to that described in Example 1, from 5-chloromethyl-1,1,3,3-tetramethyl-indane and triphenylphosphine there can be obtained [1-(1,1,3,3-tetramethyl-5-indanyl)methyl]-triphenylphosphonium chloride.

EXAMPLE 9

In a manner analogous to that described in Example 1, from [1-(1,1,3,3-tetramethyl-5-indanyl)ethyl]-triphenylphosphonium bromide and 4-acetyl-benzaldehyde there can be obtained 4'-[(E)-2-(1,1,3,3-tetramethyl-5-indanyl)propenyl]-acetophenone of melting point 130°-131° C.

EXAMPLE 10

49 g of p-[(E)-2-(5,6,7,8-tetrahydro-5,5,8,8-tetramethyl-2-naphthyl)propenyl]-benzoic acid ethyl ester (prepared as described in Example 3) are dissolved in 500 ml of ethanol at 45° C. and the resulting solution is treated dropwise while stirring with a solution of 20 g of potassium hydroxide in 50 ml of water. The mixture is stirred at 55° C. for 18 hours, then cooled, introduced into ice/water, acidified to pH 2 with 3-N sulphuric acid and extracted twice with methylene chloride. The methylene chloride extract is washed with a saturated sodium chloride solution, dried over anhydrous sodium sulphate and concentrated under reduced pressure. The residual p-[(E)-2-(5,6,7,8-tetrahydro-5,5,8,8-tetramethyl-2-naphthyl)propenyl]-benzoic acid melts at 247°–248° C. after recrystallisation from methylene chloride/hexane.

EXAMPLE 11

Into a suspension of 7.0 g of p-[(E)-2-(5,6,7,8-tetrahydro-5,5,8,8-tetramethyl-2-naphthyl)propenyl]-benzoic acid (prepared as described in Example 10) in 40 ml of absolute ether are introduced dropwise, after addition of 1.8 ml of pyridine, while stirring at 0°–5° C. 3.5 ml of thionyl chloride. After the addition of 5 drops of N,N-dimethylformamide, the solution is warmed to room temperature, stirred for 18 hours and then decanted off. The clear yellow solution of the acid chloride is introduced dropwise under argon into a solution of 3 ml of ethylamine in 20 ml of absolute ether. The mixture is stirred at room temperature for 2 hours, then introduced into a saturated sodium chloride solution and extracted twice with ether. The ether extract is washed with a saturated sodium chloride solution, dried over anhydrous sodium sulphate and evaporated under reduced pressure. The residual p-[(E)-2-(5,6,7,8-tetrahydro-5,5,8,8-tetramethyl-2-naphthyl)propenyl]-benzoic acid monoethylamide melts at 177°–178.5° C. after recrystallisation from methylene chloride/hexane.

EXAMPLE 12

11.3 g of p-[(E)-2-(5,6,7,8-tetrahydro-5,5,8,8-tetramethyl-2-naphthyl)propenyl]-benzoic acid ethyl ester (prepared as described in Example 3) dissolved in 20 ml of absolute ether and 20 ml of absolute tetrahydrofuran are introduced dropwise at 0°–5° C. into a suspension of 1.33 g of lithium aluminium hydride in 20 ml of absolute ether. The solution is stirred at room temperature for 12 hours under an inert gas, then treated dropwise at 0°–5° C. with 5 ml of a saturated sodium sulphate solution and filtered over Speedex. The filtrate is diluted with ether and washed once with a saturated sodium bicarbonate solution and twice with a saturated sodium chloride solution, dried over sodium sulphate and concentrated under reduced pressure. The separated p-[(E)-2-(5,6,7,8-tetrahydro-5,5,8,8-tetramethyl-2-naphthyl)propenyl]-benzyl alcohol melts at 123°–124° C. after recrystallisation from methanol/ether.

EXAMPLE 13

5.8 ml of acetyl chloride are introduced dropwise at ca 5° C. while stirring into a suspension of 6.6 g of p-[(E)-2-(5,6,7,8-tetrahydro-5,5,8,8-tetramethyl-2-naphthyl)propenyl]-benzyl alcohol (prepared as described in Example 12) in 10 ml of ether and 10 ml of pyridine. The mixture is stirred at room temperature for 3 hours, then introduced into ca 100 ml of ice/water and extracted three times with ether. The ether extract is washed once with 1-N hydrochloric acid and three times with a saturated sodium chloride solution, dried over sodium sulphate and concentrated under reduced pressure. The separated p-[(E)-2-(5,6,7,8-tetrahydro-5,5,8,8-tetramethyl-2-naphthyl)propenyl]-benzyl acetate melts at 100°–101° C. after recrystallisation from ether.

EXAMPLE 14

5.0 g of p-[(E)-2-(5,6,7,8-tetrahydro-5,5,8,8-tetramethyl-2-naphthyl)propenyl]-benzyl alcohol (prepared as described in Example 12) dissolved in 25 ml of dimethylformamide are introduced into a solution of 0.4 g of sodium hydride in 10 ml of dimethylformamide. After stirring at room temperature for 1 hour, the mixture is treated with 4.3 g of methyl iodide and the resulting mixture is stirred for a further 2 hours. The solution is then introduced into ca 200 ml of ice/water and extracted three times with ether. The ether extract is washed three times with a saturated sodium chloride solution, dried over sodium sulphate and concentrated under reduced pressure. The separated p-[(E)-2-(5,6,7,8-tetrahydro-5,5,8,8-tetramethyl-2-naphthyl)propenyl]-benzyl methyl ether melts at 55°–56° C. after recrystallisation from ether.

EXAMPLE 15

3.48 g of p-[(E)-2-(5,6,7,8-tetrahydro-5,5,8,8-tetramethyl-2-naphthyl)propenyl]-benzoic acid (prepared as described in Example 10) are suspended in 12 ml of toluene. After the addition of 3.57 g of thionyl chloride, the suspension is stirred at 50° C. for 12 hours and then evaporated to dryness under reduced pressure. The residue is dissolved in 6 ml of methylene chloride. The solution is introduced dropwise at 0° C. into a solution of 2.3 g of 2-amino-2-methyl-1-propanol in 6 ml of methylene chloride. The white suspension is stirred at room temperature for 2.5 hours, diluted with ethyl acetate, washed three times with water, dried over sodium sulphate and concentrated under reduced pressure. The white crystalline residue is suspended in 20 ml of ether and treated dropwise at 0° C. with 6 g of thionyl chloride. The white suspension is stirred at room temperature for 30 minutes and then treated cautiously with a saturated sodium carbonate solution until the pH value amounts to ca 9. The now clear solution is diluted with ether. The ether phase is washed three times with a saturated sodium chloride solution, dried over sodium sulphate and evaporated under reduced pressure. The residual 2-[p-[(E)-2-(5,6,7,8-tetrahydro-5,5,8,8-tetramethyl-2-naphthyl)propenyl]-phenyl]-4,4-dimethyl-2-oxazoline melts at 115°–116° C. after recrystallisation from ether.

EXAMPLE 16

In a manner analogous to that described in Example 1, from [1-(5,6,7,8-tetrahydro-5,5,8,8-tetramethyl-2-naphthyl)propyl]-triphenylphosphonium bromide and 4-ethoxycarbonyl-benzaldehyde there can be obtained p-[(E)-2-(5,6,7,8-tetrahydro-5,5,8,8-tetramethyl-2-naphthyl)-1-butenyl]-benzoic acid ethyl ester of melting point 82°–83° C.

The [1-(5,6,7,8-tetrahydro-5,5,8,8-tetramethyl-2-naphthyl)propyl]-triphenylphosphonium bromide used as the starting material can be obtained in a manner analogous to that described in Example 1 from 5,6,7,8- tetrahydro-5,5,8,8-tetramethyl-naphthalene and propionic acid chloride.

EXAMPLE 17

In a manner analogous to that described in Example 11, from p-[(E)-2-(5,6,7,8-tetrahydro-5,5,8,8-tetramethyl-2-naphthyl)propenyl]-benzoic acid and diethylamine there can be obtained p-[(E)-2-(5,6,7,8-tetrahydro-5,5,8,8-tetramethyl-2-naphthyl)propenyl]-benzoic acid diethylamide of melting point 111°–112° C.

EXAMPLE 18

In a manner analogous to that described in Example 11, from p-[(E)-2-(5,6,7,8-tetrahydro-5,5,8,8-tetramethyl-2-naphthyl)propenyl]-benzoic acid and morpholine there can be obtained p-[(E)-2-(5,6,7,8-tetrahydro-5,5,8,8-tetramethyl-2-naphthyl)propenyl]-benzoic acid morpholide of melting point 143°–144° C.

EXAMPLE 19

In a manner analogous to that described in Example 11, from p-[(E)-2-(5,6,7,8-tetrahydro-5,5,8,8-tetramethyl-2-naphthyl)propenyl]-benzoic acid and isopropanol there can be obtained p-[(E)-2-(5,6,7,8-tetrahydro-5,5,8,8-tetramethyl-2-naphthyl)propenyl]-benzoic acid isopropyl ester of melting point 119°–120° C.

EXAMPLE 20

In a manner analogous to that described in Example 11, from p-[(E)-2-(5,6,7,8-tetrahydro-5,5,8,8-tetramethyl-2-naphthyl)propenyl]-benzoic acid and 2-diethylamino-ethanol there can be obtained p-[(E)-2-(5,6,7,8-tetrahydro-5,5,8,8-tetramethyl-2-naphthyl)-propenyl]-benzoic acid 2-diethylamino-ethyl ester of melting point 65°–66° C.

EXAMPLE 21

6.7 g of p-[(E)-2-(5,6,7,8-tetrahydro-5,5,8,8-tetramethyl-2-naphthyl)propenyl]-benzyl alcohol (prepared as described in Example 12) dissolved in 100 ml of absolute ether are added dropwise within 10 minutes to a stirred suspension, cooled to 0°–5° C., of manganese dioxide in 100 ml of absolute ether. The mixture is stirred at room temperature overnight and then filtered through Celite. The filtrate is concentrated to dryness on a rotary evaporator. The yellowish oil crystallizes. Recrystallisation from ether yields p-[(E)-2-(5,6,7,8-tetrahydro-5,5,8,8-tetramethyl-2-naphthyl)propenyl]-benzaldehyde in the form of colourless crystals of melting point 140°–141° C.

EXAMPLE 22

In a manner analogous to that described in Example 1, from [1-(5,6,7,8-tetrahydro-5,5,8,8-tetramethyl-2-naphthyl)ethyl]-triphenylphosphonium bromide and 4-acetyl-benzaldehyde there can be obtained 4'-[(E)-2-(5,6,7,8-tetrahydro-5,5,8,8-tetramethyl-2-naphthyl)-propenyl]-acetophenone of melting point 148°–149° C.

EXAMPLE 23

3.0 g of 4'-[(E)-2-(5,6,7,8-tetrahydro-5,5,8,8-tetramethyl-2-naphthyl)propenyl]-acetophenone (prepared as described in Example 22) dissolved in 40 ml of benzene are treated with a catalytic amount of p-toluenesulphonic acid and 0.6 g of ethyleneglycol and warmed in a Dean-Stark apparatus, the water formed being concurrently separated off. After heating under reflux for 2 days, the mixture is cooled down, introduced into ice/saturated sodium bicarbonate solution and exhaustively extracted with ether. The ether extract is washed twice with a saturated sodium chloride solution, dried over sodium sulphate and evaporated under reduced pressure to remove the solvent. The oily residue is purified by adsorption on silica gel using hexane/ether (9:1) for the elution. The 2-methyl-2-[p-[(E)-2-(5,6,7,8-tetrahydro-5,5,8,8-tetramethyl-2-naphthyl)-propenyl]-phenyl]-1,3-dioxolane obtained from the eluate melts at 122°–123° C. after recrystallisation from ether.

EXAMPLE 24

1.0 g of sodium borohydride is cautiously added portionwise at 0°–5° C. to 10.4 g of 4'-[(E)-2-(5,6,7,8-tetrahydro-5,5,8,8-tetramethyl-2-naphthyl)propenyl]-acetophenone (prepared as described in Example 22) dissolved in 100 ml of absolute methanol. The solution is stirred at 0° C. for 1 hour and at room temperature for 2 hours, then introduced into ice/water and exhaustively extracted with ether. The ether solution is washed twice with a saturated sodium chloride solution, dried over sodium sulphate and concentrated under reduced pressure. The separated α-methyl-p-[(E)-2-(5,6,7,8-tetrahydro-5,5,8,8-tetramethyl-2-naphthyl)propenyl]-benzyl alcohol melts at 121°–123° C. after crystallisation from ether.

EXAMPLE 25

In a manner analogous to that described in Example 14, from α-methyl-p-[(E)-2-(5,6,7,8-tetrahydro-5,5,8,8-tetramethyl-2-naphthyl)propenyl]-benzyl alcohol there can be obtained 1,2,3,4-tetrahydro-6-[(E)-p-(1-methoxyethyl)-α-methyl-styryl]-1,1,4,4-tetramethylnaphthalene of melting point 88°–89° C.

EXAMPLE 26

In a manner analogous to that described in Example 13, from α-methyl-p-[(E)-2-(5,6,7,8-tetrahydro-5,5,8,8-tetramethyl-2-naphthyl)propenyl]-benzyl alcohol there can be obtained α-methyl-p-[(E)-2-(5,6,7,8-tetrahydro-5,5,8,8-tetramethyl-2-naphthyl)propenyl]-benzyl acetate of melting point 85°–86° C.

EXAMPLE 27

In a manner analogous to that described in Example 1, from [1-(5,6,7,8-tetrahydro-5,5,8,8-tetramethyl-2-naphthyl)ethyl]-triphenylphosphonium bromide and 4-methyl-benzaldehyde there can be obtained 6-[(E)-p,α-dimethylstyryl]-1,2,3,4-tetrahydro-1,1,4,4-tetramethylnaphthalene of melting point 84°–85° C.

EXAMPLE 28

In a manner analogous to that described in Example 1, from [1-(5,6,7,8-tetrahydro-5,5,8,8-tetramethyl-2-naphthyl)ethyl]-triphenylphosphonium bromide and 4-isopropyl-benzaldehyde there can be obtained 6-[(E)-p-isopropyl-α-methylstyryl]-1,2,3,4-tetrahydro-1,1,4,4-tetramethylnaphthalene of melting point 86°–87° C.

EXAMPLE 29

In a manner analogous to that described in Example 1, from [1-(5,6,7,8-tetrahydro-5,5,8,8-tetramethyl-2-naphthyl)ethyl]-triphenylphosphonium bromide and 2,4-dimethyl-benzaldehyde there can be obtained 6-[(E)-α,2,4-trimethylstyryl]-1,2,3,4-tetrahydro-1,1,4,4-tetramethylnaphthalene of melting point 54°–56° C.

EXAMPLE 30

In a manner analogous to that described in Example 1, but preferably with a longer reaction time, from methyl-triphenylphosphonium bromide and p-[(E)-2-(5,6,7,8-tetrahydro-5,5,8,8-tetramethyl-2-naphthyl)-propenyl]-benzaldehyde (prepared as described in Example 21) there can be obtained 1,2,3,4-tetrahydro-1,1,4,4-tetramethyl-6-[(E)-α-methyl-p-vinylstyryl]naphthalene of melting point 94°–95° C.

EXAMPLE 31

In a manner analogous to that described in Example 1, but preferably with a longer reaction time, from ethyl-triphenylphosphonium bromide and p-[(E)-2-(5,6,7,8-tetrahydro-5,5,8,8-tetramethyl-2-naphthyl)-propenyl]-benzaldehyde (prepared as described in Example 21) there can be obtained 1,2,3,4-tetrahydro-1,1,4,4-tetramethyl-6-[(E)-α-methyl-p-allylstyryl]naphthalene of melting point 64°–66° C.

EXAMPLE 32

2 g of p-[(E)-2-(5,6,7,8-tetrahydro-5,5,8,8-tetramethyl-2-naphthyl)propenyl]-benzaldehyde (prepared as described in Example 21) and 1.4 g of diethylphosphonacetic acid ethyl ester are dissolved in 5 ml of dimethylformamide. A sodium alcoholate solution (prepared using 6.16 g of sodium in 3 ml of absolute alcohol) is added thereto at room temperature while stirring. After stirring at room temperature for 18 hours, the mixture is poured into ice-cold 1-N hydrochloric acid and exhaustively extracted with ether. The ether phases are washed with saturated sodium bicarbonate solution and sodium chloride solution and, after drying over anhydrous sodium sulphate, are concentrated under reduced pressure. The residue is purified by adsorption on silica gel using hexane/ether (19:1) for the elution. The (E)-p-[(E)-2-(5,6,7,8-tetrahydro-5,5,8,8-tetramethyl-2-naphthyl)propenyl]-cinnamic acid ethyl ester obtained from the eluate melts at 126°–127° C. after recrystallisation from hexane/ether.

EXAMPLE 33

In a manner analogous to that described in Example 11, from p-[(E)-2-(5,6,7,8-tetrahydro-5,5,8,8-tetramethyl-2-naphthyl)propenyl]-benzoic acid and benzyl chloride there can be obtained p-[(E)-2-(5,6,7,8-tetrahydro-5,5,8,8-tetramethyl-2-naphthyl)propenyl]-benzoic acid benzyl ester of melting point 113°–114° C.

EXAMPLE 34

In a manner analogous to that described in Example 11, from p-[(E)-2-(5,6,7,8-tetrahydro-5,5,8,8-tetramethyl-2-naphthyl)propenyl]-benzoic acid and 4-nitro-benzaldehyde there can be obtained 4-nitrobenzyl p-[(E)-2-(5,6,7,8-tetrahydro-5,5,8,8-tetramethyl-2-naphthyl)-propenyl]-benzoate of melting point 183°–184° C.

EXAMPLE 35

In a manner analogous to that described in Example 11, from p-[(E)-2-(5,6,7,8-tetrahydro-5,5,8,8-tetramethyl-2-naphthyl)propenyl]-benzoic acid and ethyleneglycol there can be obtained 2-hydroxyethyl p-[(E)-2-(5,6,7,8-tetrahydro-5,5,8,8-tetramethyl-2-naphthyl)-propenyl]-benzoate of melting point 138°–139° C.

EXAMPLE 36

60 ml of a 20% solution of dibutylaluminium hydride in hexane are added dropwise at room temperature under an inert gas atmosphere and while stirring to a solution of 14.1 g of p-[(E)-2-(5,6,7,8-tetrahydro-5,5,8,8-tetramethyl-2-naphthyl)propenyl]-(E)-cinnamic acid ethyl ester (prepared as described in Example 32) in 70 ml of absolute hexane and the mixture is stirred overnight. The solution is then treated dropwise at 0°–5° C. with 50 ml of methanol and filtered over Speedex. The filtrate is diluted with ether, washed once with a saturated sodium bicarbonate solution and twice with a saturated sodium chloride solution, dried over sodium sulphate and concentrated under reduced pressure. The separated 3-p-[[(E)-2-(5,6,7,8-tetrahydro-5,5,8,8-tetramethyl-2-naphthyl)propenyl]phenyl]-(E)-2-propen-1-ol melts at 109°–110° C. after recrystallisation from hexane.

EXAMPLE 37

In a manner analogous to that described in Example 13, from 3-p-[[(E)-2-(5,6,7,8-tetrahydro-5,5,8,8-tetramethyl-2-naphthyl)propenyl]phenyl]-(E)-2-propan-1-ol there can be obtained 3-p-[[(E)-2-(5,6,7,8-tetrahydro-5,5,8,8-tetramethyl-2-naphthyl)propenyl]phenyl]-2-propen-1-yl acetate of melting point 109°–110° C.

EXAMPLE 38

In a manner analogous to that described in Example 14, from 3-p-[[(E)-2-(5,6,7,8-tetrahydro-5,5,8,8-tetramethyl-2-naphthyl)propenyl]phenyl]-(E)-2-propen-1-ol there can be obtained 3-p-[[(E)-2-(5,6,7,8-tetrahydro-5,5,8,8-tetramethyl-2-naphthyl)propenyl]phenyl]-2-propen-1-yl methyl ether of melting point 88°–90° C.

The following Examples illustrate pharmaceutical preparations provided by the invention:

EXAMPLE A

Capsules for oral administration can contain the following ingredients:

|  | Per capsule |
| --- | --- |
| p-[(E)-2-(5,6,7,8-Tetrahydro-5,5,8,8-tetramethyl-2-naphthyl)-propenyl]-benzoic acid ethyl ester | 0.1 mg |
| Wax mixture | 50.5 mg |
| Vegetable oil | 98.9 mg |
| Trisodium salt of ethylenediaminetetraacetic acid | 0.5 mg |

EXAMPLE B

An ointment can have the following composition:

| p-[(E)-2-(5,6,7,8-Tetrahydro-5,5,8,8-tetramethyl-2-naphthyl)-propenyl]-benzoic acid ethyl ester | 0.01 g |
| --- | --- |
| Cetyl alcohol | 2.7 g |
| Lanolin | 6.0 g |
| Vaseline | 15.0 g |
| Distilled water q.s. ad | 100.0 g |

I claim:
1. Compounds of the formula:

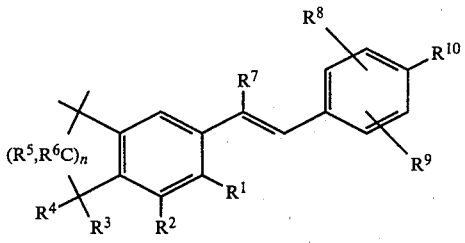

wherein n is an integer of from 1 and 2 and, when n is 1, $R^1$ and $R^2$ are individually hydrogen, lower alkoxy or halogen, or, when n is 2, $R^1$ is hydrogen, lower alkoxy or halogen and $R^2$ is hydrogen; $R^3$, $R^4$, $R^5$ and $R^6$ are individually hydrogen or lower alkyl; $R^7$ is hydrogen, methyl or ethyl; $R^8$ and $R^9$ are hydrogen, lower alkyl or halogen; and $R^{10}$ is $-(CH=CR^{19})_m R^{11}$; m is zero or 1; $R^{11}$ is

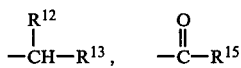

or 2-oxazolinyl, or, when m is 1, $R^{11}$ is additionally hydrogen; $R^{12}$ is hydrogen or lower alkyl; $R^{13}$ is hydrogen, lower alkyl, $-N(R^{17}, R^{18})$ or $-OR^{14}$; $R^{14}$ is hydrogen, lower alkyl or alkanoyl; $R^{15}$ is hydrogen, lower alkyl, $-OR^{16}$ or $-(CH_2)_p N(R^{17}, R^{18})$; $R^{16}$ is hydrogen, lower alkyl, hydroxy-(lower alkyl), aryl, substituted aryl, aralkyl or aralkyl substituted in the aryl portion; $R^{17}$ and $R^{18}$ are individually hydrogen or lower alkyl or $R^{17}$ and $R^{18}$ taken together with the nitrogen atom to which they are attached form a heterocyclic group; $R^{19}$ is hydrogen or lower alkyl and p is zero, 1, 2 or 3; as well as ketals thereof where $R^{11}$ is $-C(O)R^{15}$ and $R^{15}$ is hydrogen or lower alkyl, as well as salts thereof.

2. Compounds according to claim 1 in which, when n stands for 1, $R^1$ and $R^2$ represent hydrogen, lower alkoxy or halogen, or, when n stands for 2, $R^1$ represents hydrogen, lower alkoxy or halogen and $R^2$ represents hydrogen; $R^3$, $R^4$, $R^5$ and $R^6$ represent hydrogen or lower alkyl; $R^7$ represents hydrogen, methyl or ethyl; $R^8$ and $R^9$ represent hydrogen, lower alkyl or halogen; and $R^{10}$ represents hydroxymethyl, alkoxymethyl, alkanoyloxymethyl, carboxyl, alkoxycarbonyl, formyl, alkylenedioxymethyl, alkanoyl, carbamoyl, mono(-lower alkyl)carbamoyl, di(lower alkyl)carbamoyl, N-heterocyclylcarbonyl or 2-oxazolinyl, and salts thereof.

3. The compounds of claim 1, wherein n stands for 2.

4. The compounds of claim 3, wherein $R^1$, $R^2$, $R^5$, $R^6$, $R^8$ and $R^9$ represent hydrogen and $R^3$, $R^4$ and $R^7$ represent methyl.

5. The compound of claim 1 wherein $R^{11}$ is

6. The compound of claim 5 wherein $R^{15}$ is hydrogen or lower alkyl.

7. The compound of claim 6 wherein said compound is 4'-[(E)-2-(1,1,3,3-tetramethyl-5-indanyl)propenyl]-acetophenone.

8. The compound of claim 6 wherein said compound is p-[(E)-2-(5,6,7,8-tetrahydro-5,5,8,8-tetramethyl-2-naphthyl)propenyl]-benzaldehyde.

9. The compound of claim 6 wherein said compound is 4'-[(E)-2-(5,6,7,8-tetrahydro-5,5,8,8-tetramethyl-2-naphthyl)propenyl]-acetophenone.

10. The compound of claim 6 wherein said compound is 3-p-[[(E)-2-(5,6,7,8-tetrahydro-5,5,8,8-tetramethyl-2-naphthyl)propenyl]phenyl]-2-propen-1-yl acetate.

11. The compound of claim 5 wherein $R^{15}$ is $-(CH_2)_p N(R^{17}, R^{18})$.

12. The compound of claim 11 wherein said compound is p-[(E)-2-(5,6,7,8-tetrahydro-5,5,8,8-tetramethyl-2-naphthyl)-propenyl]-benzoic acid diethylamide.

13. The compound of claim 11 wherein said compound is p-[(E)-2-(5,6,7,8-tetrahydro-5,5,8,8-tetramethyl-2-naphthyl)-propenyl]-benzoic acid monoethylamide.

14. The compound of claim 11 wherein said compound is D-[(E)-2-(5,6,7,8-tetrahydro-2-naphthyl)-propenyl]-benzoic acid morpholide.

15. The compound of claim 1 wherein R' is

16. The compound of claim 15 wherein $R^{13}$ is hydrogen or lower alkyl.

17. The compound of claim 16 wherein said compound is 6-[(E)-p,α-dimethylstyryl]-1,2,3,4-tetrahydro-1,1,4,4-tetramethyl-naphthalene.

18. The compound of claim 16 wherein said compound is 6-[(E)-p-isopropyl-α-methylstyryl]-1,2,3,4-tetrahydro-1,1,4,4-tetramethylnaphthalene.

19. The compound of claim 16 wherein said compound is 6-[(E)-α,2,4-trimethylstyryl]-1,2,3,4-tetrahydro-1,1,4,4-tetramethyl-naphthalene.

20. The compound of claim 16 wherein said compound is 1,2,3,4-tetrahydro-1,1,4,4-tetramethyl-6-[(E)-α-methyl-p-allylstryl]-naphthalene.

21. The compound of claim 15 wherein $R^{13}$ is $-N(R^{17}, R^{18})$ or $OR^{14}$.

22. The compound of claim 21 wherein said compound is p-[(E)-2-(5,6,7,8-Tetrahydro-5,5,8,8-tetramethyl-2-naphthyl)propenyl]-benzyl methyl ester.

23. The compound of claim 21 wherein said compound is p-[(E)-2-(5,6,7,8-Tetrahydro-5,5,8,8-tetramethyl-2-naphthyl)propenyl]-benzyl acetate.

24. The compound of claim 21 wherein said compound is p-[(E)-2-(5,6,7,8-tetrahydro-5,5,8,8-tetramethyl-2-naphthyl)propenyl]-benzyl alcohol.

25. The compound of claim 21 wherein said compound is α-methyl-p-[(E)-2-(5,6,7,8-tetrahydro-5,5,8,8-tetramethyl-2-naphthyl)propenyl]-benzyl alcohol.

26. The compound of claim 1 wherein $R^{11}$ is 2-oxazolinyl.

27. The compound of claim 26 wherein said compound is 2-[p-[(E)-2-(5,6,7,8-tetrahydro-5,5,8,8-tetramethyl-2-naphthyl)propenyl]phenyl]-4,4-dimethyl-2-oxazoline.

28. The compound of claim 1 wherein $R^{11}$ is hydrogen.

29. The compound of claim 28 wherein said compound is 1,2,3,4-tetrahydro-1,1,4,4-tetramethyl-6-[(E)-α-methyl-p-vinylstyryl]naphthalene.

30. Compounds of the formula:

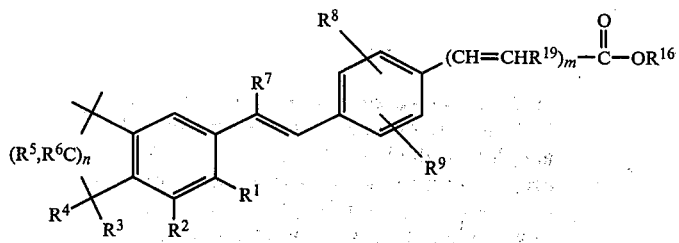

wherein n is an integer of from 1 and 2 and, when n is 1, $R^1$ and $R^2$ are individually hydrogen, lower alkoxy or halogen, or, when n is 2, $R^1$ is hydrogen, lower alkoxy or halogen and $R^2$ is hydrogen; $R^3$, $R^4$, $R^5$ and $R^6$ are individually hydrogen or lower alkyl; $R^7$ is hydrogen, methyl or ethyl; $R^8$ and $R^9$ are hydrogen, lower alkyl or halogen; m is zero or 1; $R^{16}$ is hydrogen, lower alkyl, hydroxy-(lower alkyl), aryl, substituted aryl, aralkyl or aralkyl substituted in the aryl portion; $R^{19}$ is hydrogen or lower alkyl; as well as salts thereof.

31. The compound of claim 30 wherein $R^{16}$ is lower alkyl.

32. The compound of claim 31 wherein said compound is p-[(E)-2-(3-Methoxy-5,6,7,8-tetrahydro-5,5,8,8-tetramethyl-2-naphthyl)propenyl]-benzoic acid ethyl ester.

33. The compound of claim 31 wherein said compound is p-[(E)-2-(1,1,3,3-tetramethyl-5-indanyl)-propenyl]-benzoic acid ethyl ester.

34. The compound of claim 31 wherein said compound is p-[(E)-2-(7-methoxy-1,1,3,3-tetramethyl-5-indanyl)propenyl]-benzoic acid ethyl ester.

35. The compound of claim 31 wherein said compound is p-[(E)-2-(5,6,7,8-tetrahydro-5,5,8,8-tetramethyl-2-naphthyl)propenyl]-2-methyl-benzoic acid ethyl ester.

36. The compound of claim 30 wherein $R^{16}$ is hydrogen.

37. The compound of claim 36 wherein said compound is p-[(E)-2-(5,6,7,8-tetrahydro-5,5,8,8-tetramethyl-2-naphthyl)-propenyl]-benzoic acid.

38. The compound of claim 30 wherein $R^{16}$ is hydroxy(lower alkyl).

39. The compound of claim 38 wherein said compound is 2-hydroxyethyl p-[(E)-2-(5,6,7,8-tetrahydro-5,5,8,8-tetramethyl-2-naphthyl)-propenyl]-benzoate.

40. The compound of claim 30 where $R^{16}$ is aryl, aralkyl, substituted aryl, or substituted arylalkyl.

41. The compound of claim 40 wherein said compound is p-[(E)-2-(5,6,7,8-tetrahydro-5,5,8,8-tetramethyl-2-naphthyl)propenyl]-benzoic acid benzyl ester.

42. The compound of claim 40 wherein said compound is 4-nitrobenzyl p-[(E)-2-(5,6,7,8-tetrahydro-5,5,8,8-tetramethyl-2-naphthyl)propenyl]-benzoate.

43. The compound of claim 31 wherein said compound is p-[(E)-2(5,6,7,8-tetrahydro-5,5,8,8-tetramethyl-2-naphthyl)propenyl]benzoic acid ethyl ester.

44. A pharmaceutical preparation comprising a compound of the formula:

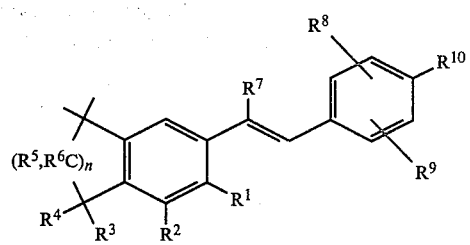

wherein n is an integer of from 1 and 2 and, when n is 1, $R^1$ and $R^2$ are individually hydrogen, lower alkoxy or halogen, or, when n is 2, $R^1$ is hydrogen, lower alkoxy or halogen and $R^2$ is hydrogen; $R^3$, $R^4$, $R^5$ and $R^6$ are individually hydrogen or lower alkyl; $R^7$ is hydrogen, methyl or ethyl; $R^8$ and $R^9$ are hydrogen, lower alkyl or halogen; and $R^{10}$ is —(CH=CR$^{19}$)$_m$R$^{11}$; m is zero or 1; $R^{11}$ is

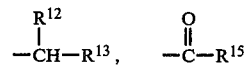

or 2-oxazolinyl, or, when m is 1, $R^{11}$ is additionally hydrogen; $R^{12}$ is hydrogen or lower alkyl; $R^{13}$ is hydrogen, lower alkyl, —N($R^{17}$, $R^{18}$) or —OR$^{14}$; $R^{14}$ is hydrogen, lower alkyl or alkanoyl; $R^{15}$ is hydrogen, lower alkyl, —OR$^{16}$ or —(CH$_2$)$_p$N($R^{17}$, $R^{18}$); $R^{16}$ is hydrogen, lower alkyl, hydroxy-(lower alkyl), aryl, substituted aryl, aralkyl or aralkyl substituted in the aryl portion; $R^{17}$ and $R^{18}$ are individually hydrogen or lower alkyl or $R^{17}$ and $R^{18}$ taken together with the nitrogen atom to which they are attached form a heterocyclic group; $R^{19}$ is hydrogen or lower alkyl and p is zero, 1, 2 or 3; as well as ketals thereof where $R^{11}$ is —C(O)R$^{15}$ and $R^{15}$ is hydrogen or lower alkyl, or a salt thereof and an inert pharmaceutically effective carrier.

45. The pharmaceutical preparation of claim 44 wherein said compound p-[(E)-2-(3-methoxy-5,6,7,8-tetrahydro-5,5,8,8-tetramethyl-2-naphthyl)-propenyl]-benzoic acid ethyl ester.

46. The pharmaceutical preparation of claim 44 wherein said compound is p-[(E)-2-(5,6,7,8-tetrahydro-5,5,8,8-tetramethyl-2-naphthyl)propenyl]-benzyl methyl ether.

47. The process of treating neoplasms, dermatological conditions or rheumatic illness comprising administering to a patient a composition containing an effective amount of a compound of the formula:

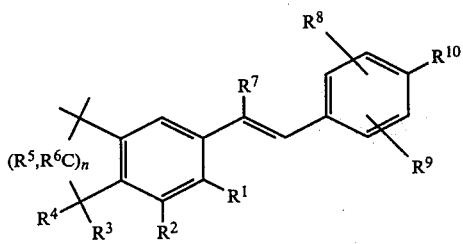

wherein n is an integer of from 1 and 2 and, when n is 1, $R^1$ and $R^2$ are individually hydrogen, lower alkoxy or halogen, or, when n is 2, $R^1$ is hydrogen, lower alkoxy or halogen and $R^2$ is hydrogen; $R^3$, $R^4$, $R^5$ and $R^6$ are individually hydrogen or lower alkyl; $R^7$ is hydrogen, methyl or ethyl; $R^8$ and $R^9$ are hydrogen, lower alkyl or halogen; and $R^{10}$ is —(CH=$CR^{19}$)$_m R^{11}$; m is zero or 1; $R^{11}$ is

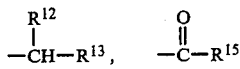

or 2-oxazolinyl, or, when m is 1, $R^{11}$ is additionally hydrogen; $R^{12}$ is hydrogen or lower alkyl; $R^{13}$ is hydrogen, lower alkyl, —N($R^{17}$, $R^{18}$) or —$OR^{14}$; $R^{14}$ is hydrogen, lower alkyl or alkanoyl; $R^{15}$ is hydrogen, lower alkyl, —$OR^{16}$ or —(CH$_2$)$_p$N($R^{17}$, $R^{18}$); $R^{16}$ is hydrogen, lower alkyl, hydroxy-(lower alkyl), aryl, substituted aryl, aralkyl or aralkyl substituted in the aryl portion; $R^{17}$ and $R^{18}$ are individually hydrogen or lower alkyl or $R^{17}$ and $R^{18}$ taken together with the nitrogen atom to which they are attached form a heterocyclic group; $R^{19}$ is hydrogen or lower alkyl and p is zero, 1, 2 or 3; as well as ketals thereof where $R^{11}$ is —C(O)$R^{15}$ and $R^{15}$ is hydrogen or lower alkyl, or a salt thereof;

and inert pharmaceutically acceptable carrier.

* * * * *